(12) United States Patent
Lee

(10) Patent No.: US 9,492,604 B2
(45) Date of Patent: Nov. 15, 2016

(54) NASAL IRRIGATION APPLIANCE

(71) Applicant: Carol Lee, Austin, TX (US)

(72) Inventor: Carol Lee, Austin, TX (US)

( * ) Notice: Subject to any disclaimer, the term of this patent is extended or adjusted under 35 U.S.C. 154(b) by 0 days.

(21) Appl. No.: 15/135,904

(22) Filed: Apr. 22, 2016

(65) Prior Publication Data
US 2016/0235907 A1 Aug. 18, 2016

Related U.S. Application Data

(63) Continuation of application No. 14/194,480, filed on Feb. 28, 2014, now Pat. No. 9,351,904.

(60) Provisional application No. 61/771,566, filed on Mar. 1, 2013.

(51) Int. Cl.
| | |
|---|---|
| *B67B 1/04* | (2006.01) |
| *A61M 3/00* | (2006.01) |
| *A61H 35/04* | (2006.01) |
| *A61M 3/02* | (2006.01) |
| *A61J 3/00* | (2006.01) |
| *A61B 17/24* | (2006.01) |
| *A61H 33/00* | (2006.01) |
| *A61K 35/08* | (2015.01) |
| *A61H 33/04* | (2006.01) |
| *C02F 103/02* | (2006.01) |

(52) U.S. Cl.
CPC .............. *A61M 3/005* (2013.01); *A61H 35/04* (2013.01); *A61M 3/0245* (2013.01); *A61M 3/0262* (2013.01); *A61B 2017/246* (2013.01); *A61H 33/0095* (2013.01); *A61H 2033/048* (2013.01); *A61H 2201/0207* (2013.01); *A61H 2201/5087* (2013.01); *A61J 3/002* (2013.01); *A61K 35/08* (2013.01); *A61M 2202/0468* (2013.01); *A61M 2205/3379* (2013.01); *A61M 2205/36* (2013.01); *A61M 2205/75* (2013.01); *A61M 2210/0618* (2013.01); *C02F 2103/026* (2013.01); *C02F 2303/04* (2013.01)

(58) Field of Classification Search
CPC .................. A61J 3/002; A61H 35/04; A61H 2201/5087; A61H 2201/0207; A61H 22/0095; A61H 2033/048; A61B 2017/246; C02F 2103/026
USPC ............... 141/18, 82; 222/108, 145.1, 145.5, 222/145.8, 146.2
See application file for complete search history.

(56) References Cited

U.S. PATENT DOCUMENTS

| | | | |
|---|---|---|---|
| 5,013,459 | A | 5/1991 | Gettings et al. |
| 7,959,597 | B2 | 6/2011 | Baker et al. |
| 7,971,761 | B1 | 7/2011 | Kudlu |
| 8,292,491 | B2 | 10/2012 | Castillo et al. |
| 2004/0245124 | A1 | 12/2004 | Hurst |
| 2008/0154183 | A1 | 6/2008 | Baker et al. |
| 2009/0110749 | A1 | 4/2009 | Norton et al. |
| 2012/0043269 | A1 | 2/2012 | Shariff et al. |

*Primary Examiner* — Jason K Niesz
(74) *Attorney, Agent, or Firm* — Matthew E. Burr

(57) ABSTRACT

An apparatus and methods for dispensing a sanitized saline solution for rinsing the nasal passages and sinuses. The disclosure includes methods for bulk storage of granular sodium salt mixtures (pH balanced sodium chloride and sodium bicarbonate), bulk storage of water, heating and sensing elements, filtering elements, and dispensing elements. The apparatus provides controls for customizing the concentration and temperature of the dispensed saline solution, and provides for dispensing the solution into a delivery device, with a water catch basin and area for drying a delivery device after use.

15 Claims, 7 Drawing Sheets

NASAL IRRIGATION APPLIANCE

CROSS-REFERENCE TO RELATED APPLICATIONS

This application is a continuation of, claims priority from and the benefit of U.S. Provisional patent application Ser. No. 61/771,566, filed Mar. 1, 2013, and co-pending U.S. Non-provisional patent application Ser. No. 14/194,480, filed Feb. 28, 2014, each having the same title and by the same inventor, the disclosures of which are incorporated herein by reference as if set forth in full.

FIELD OF THE INVENTION

This disclosure relates generally to nasal irrigation devices, and more particularly to an appliance to prepare and deliver a nasal irrigation solution to a nasal irrigation vessel.

BACKGROUND OF THE INVENTION

Nasal irrigation is a personal hygiene practice in which the nasal cavity is washed to flush out excess mucus and debris from the nose and sinuses. The practice of nasal irrigation dates back to an Ayurvedic medicine technique in ancient India. Nasal irrigation promotes good sinus and nasal health, and can provide effective relief to symptoms of facial pain, headache, halitosis, cough, anterior rhinorrhea (watery discharge) and nasal congestion. Daily saline nasal irrigation can bring relief from allergens and increase immunity to common colds and flu.

Flushing the nasal cavity with salt water moisturizes the nasal cavity and removes encrusted material. In proper proportion, nasal salt water solution with slight acidic pH functions as an anti-bacterial irrigant. The flow of salt water through the nasal passage flushes the dirt, airborne allergens (dust and pollen), pollutants and bacteria-filled mucus. Salt water flushing also loosens and thins the mucus, making it easier to expel, and allowing the cilia (hairs in the nasal passage) to function more efficiently in pushing excess mucus either to the back of the throat or to the nose to be expelled.

The source of water that is used with nasal rinsing devices is important, as tap water often contains low levels of organisms, such as microscopic amoebas. Of particular concern is the amoeba *Naegleria fowleri*, which is commonly found in the environment, including in warm freshwater lakes and rivers that supply municipal drinking water treatment plants. Primary amebic meningoencephalitis (PAM), which is usually fatal, occurs when *Naegleria fowleri*-containing water enters the nose and migrates to the brain via the olfactory nerve. The infective stage of *Naegleria fowleri* is the ameboid trophozoite cycle of its life, at which point the amoeba is 10-35 µm long.

Some manufacturers of devices currently on the market for nasal irrigation recommend using distilled water for nasal irrigation, but many users use hot tap water because it is more comfortable and convenient. In 2011, two adults died in Louisiana hospitals of PAM as a result of using tap water for regular sinus irrigation with neti pots. These were the first reported PAM cases in the United States that were associated with the presence of *Naegleria fowleri* in household plumbing served by treated municipal water. On Sep. 12, 2013 the Louisiana Department of Health and Hospitals reported that parish water in Violet and Arabi tested positive for the *Naegleria fowleri* amoeba that killed a 4-year-old Mississippi boy in August after he visited St. Bernard Parish.

According to the Center for Disease Control and Prevention, the St. Bernard Parish case was the first in which the Naegleria amoeba was found in water treated by a U.S. water system. In countries where the practice of nasal irrigation is common there has been an increase in cases of PAM that have been attributed to nasal irrigation. From 2008-2009 there were 13 patients in Karachi, Pakistan whose death from *Naegleria fowleri* meningoencephalitis was attributed to using tap water to clean their sinuses.

Devices that are currently available for nasal irrigation in a residential setting do not provide a warm or sanitized solution to use for nasal irrigation. The present invention overcomes these deficiencies by providing an appliance that allows tap water to be safely used for nasal irrigation, and optimizing the nasal irrigation experience and benefits with customizable control of the sodium concentration and temperature of the saline solution.

The Disclosures Of The Following References Are Incorporated Herein By Reference 1. Yoder, J. S., Straif-Bourgeois, S., Roy, S. L., et al. 2012. Primary Amebic Meningoencephalitis Deaths Associated With Sinus Irrigation Using Contaminated Tap Water, Clinical Infectious Diseases: cis626v1-cis626.
2. Shakoor S, Beg M A, Mahmood S F, Bandea R, Sriram R, Noman F, et al. Primary amebic meningoencephalitis caused by *Naegleria fowleri*, Karachi, Pakistan. Emerging Infectious. Diseases [serial on the Internet]. 2011 February [date cited]. http://dx.doi.org/10.3201/eid1702.100442
3. Rabago D, Guerard E, Bukstein D. Nasal irrigation for chronic sinus symptoms in patients with allergic rhinitis, asthma, and nasal polyposis. Wisconsin Medical Journal. 107(2):69-75, 2008,
4. Pynnonen M A, Mukerji S S, Kim H M, et al. Nasal saline for chronic sinonasal symptoms: a randomized controlled trial. Arch Otolaryngol Head Neck Surg. 2007; 133:1115-1120.
5. Rabago D, Barrett B, Marchand L, Maberry R, Mundt M. Qualitative aspects of nasal irrigation use by patients with chronic sinus disease in a multi-method study. Annals of Family Medicine. 2006; 4:295-301.
6. Rabago D, Pasic T, Zgierska A, Barrett B, Mundt M, Maberry R. The efficacy of hypertonic saline nasal irrigation for chronic sinonasal symptoms. Otolaryngol Head Neck Surg. 2005; 133:3-8.
7. Rabago D, Zgierska A, Mundt M, et al. Efficacy of daily hypertonic saline nasal irrigation among patients with sinusitis: a randomized controlled trial. Journal of Family Practice. 2002; 51(12):1049-1055.
8. Heatley D G, McConnell K E, Kille T L, Leverson G E. Nasal irrigation for the alleviation of sinonasal symptoms, Otolaryngol Head Neck Surgery. 125(1):44-48, 2001.

SUMMARY OF THE INVENTION

The present invention overcomes the disadvantages of current nasal irrigation products by providing an appliance that is compact and easy to use, and that allows the use of normal tap water to comfortably and safely irrigate the nasal pathways and sinuses. The advantages of the invention are provided by an apparatus and methods for heating and sterilizing a pre-determined volume of water, apparatus and methods for measuring a pre-determined volume of sodium chloride mixture, and apparatus and methods for dispensing the sodium chloride mixture and sterilized water to prepare a saline solution. While sodium chloride is preferred, it will be recognized by those skilled in the art that other salts of sodium, or mixtures of sodium salts such as sodium chloride with sodium bicarbonate, may be suitable for the saline solution. Accordingly, the invention is described herein with reference to sodium chloride and sodium chloride/sodium bicarbonate mixtures for illustrative and not limiting purposes. It will be further understood that references to sodium herein refer to salts of sodium and not the elemental metal.

In one aspect of the present invention, a counter-top appliance is provided having a housing, a storage tank for water, a sensor such as a flowmeter to measure a volume of water, a water heating chamber, a water filtration system with aseptic dispense valve, a compartment for storing a bulk granular sodium chloride mixture, a device for measuring specific amounts of the sodium chloride mixture, a main dispensing unit for delivering the sodium chloride mixture and disinfected heated water, and a catch basin with tray. An optional device for agitating the dispensed sodium and water also is included.

The methods include steps for storing a bulk quantity of granular sodium chloride and sodium bicarbonate mixture and dispensing a customizable amount of the mixture through the main dispensing unit of the appliance. The methods further include steps for storing non-sterile water and pumping an amount appropriate for one nasal irrigation, heating the water to a customizable temperature, filtering the water to remove protozoa and amoeba, and dispensing the sterilized water through an aseptic dispense valve within the main dispensing unit of the appliance.

The apparatus provides a storage and dispensing receptacle for storing a bulk quantity of granular sodium chloride and sodium bicarbonate mixture and delivering a pre-determined amount of the bulk mixture into a dispensing unit. In a preferred embodiment, the bulk storage receptacle has an interior slope that guides the sodium mixture into the measuring device, and the storage receptacle lid provides an element for moisture absorption to enhance the free flow of the bulk mixture to the measuring device. A measuring device is provided to deliver a pre-determined amount of the bulk sodium mixture for dispensing, and allows for user control of the sodium concentration within tolerances of producing an isotonic solution (0.9% sodium chloride per mL of water) or hypertonic solution (>0.9% sodium chloride per mL of water). The selected amount of sodium mixture is collected in a Dosage Cartridge and is then released to the main dispensing unit of the appliance into a user-provided nasal irrigation vessel.

The apparatus further provides a receptacle for storing tap water and pumping a predetermined quantity of water to a heating chamber. The apparatus control panel allows the user to control the temperature within tolerances safe for nasal irrigation, and to control the volume of water to be heated and dispensed as appropriate for pediatric use (120 mL of water) or adult use (120 mL to 240 mL of water). A filter with a minimum absolute 1 micron porosity, for example, sanitizes the water prior to releasing it through an aseptic dispense valve of the main dispensing unit. Through heating and filtration elements of the apparatus, disinfected water is delivered at a customizable temperature from the main dispensing unit of the appliance into a user-provided nasal irrigation vessel.

The main dispensing unit of the appliance contains a conveyor from the sodium Dosage Cartridge to deliver the sodium to the nasal irrigation vessel, and an aseptic dispense valve to deliver the warm, filtered water to the user-provided nasal irrigation vessel. An optional agitation wand is provided to allow the user to thoroughly mix the sodium and sanitized water to ensure a homogenous solution. A receptacle such as a tray below the main dispensing units holds a catch basin that indicates where the sodium mixture and sanitized water will be dispensed, and is capable of retaining a dosage of the sodium mixture and at least one volume of liquid dispensed from the appliance. An indicator shows when the basin is full. Design elements allow for easy removal of the tray and emptying of the basin. The tray also can serve as an area for drying a nasal irrigation delivery vessel. Optionally, the tray area of the appliance may be enclosed and equipped with Ultraviolet (UV) light to aid with sterilizing the nasal irrigation delivery vessel.

In other exemplary embodiments of the present invention, the functions and sizing of the components may be modified to provide different models of the appliance as appropriate to different users and needs. For example, in an embodiment specific for pediatric use, the size of the tap water storage tank and the water heating chamber would be smaller than in a model for adult use, and the controls for the volume of water and dosage of sodium chloride would be more limited for the pediatric embodiments. Another exemplary embodiment of the appliance eliminates the water filtration component for users who prefer to use purified water (rather than tap water) in the water storage tank yet desire the benefits of automatically dosing the sodium chloride mixture, heating the water to the desired temperature, and dispensing both to the nasal irrigation vessel.

BRIEF DESCRIPTION OF THE DRAWINGS

For a more complete understanding of the present disclosure, and the advantages thereof, reference is now made to the following descriptions taken in conjunction with the accompanying drawings, in which.

PROCESS DESCRIPTION OF THE NASAL IRRIGATION APPLIANCE

Figure 1:
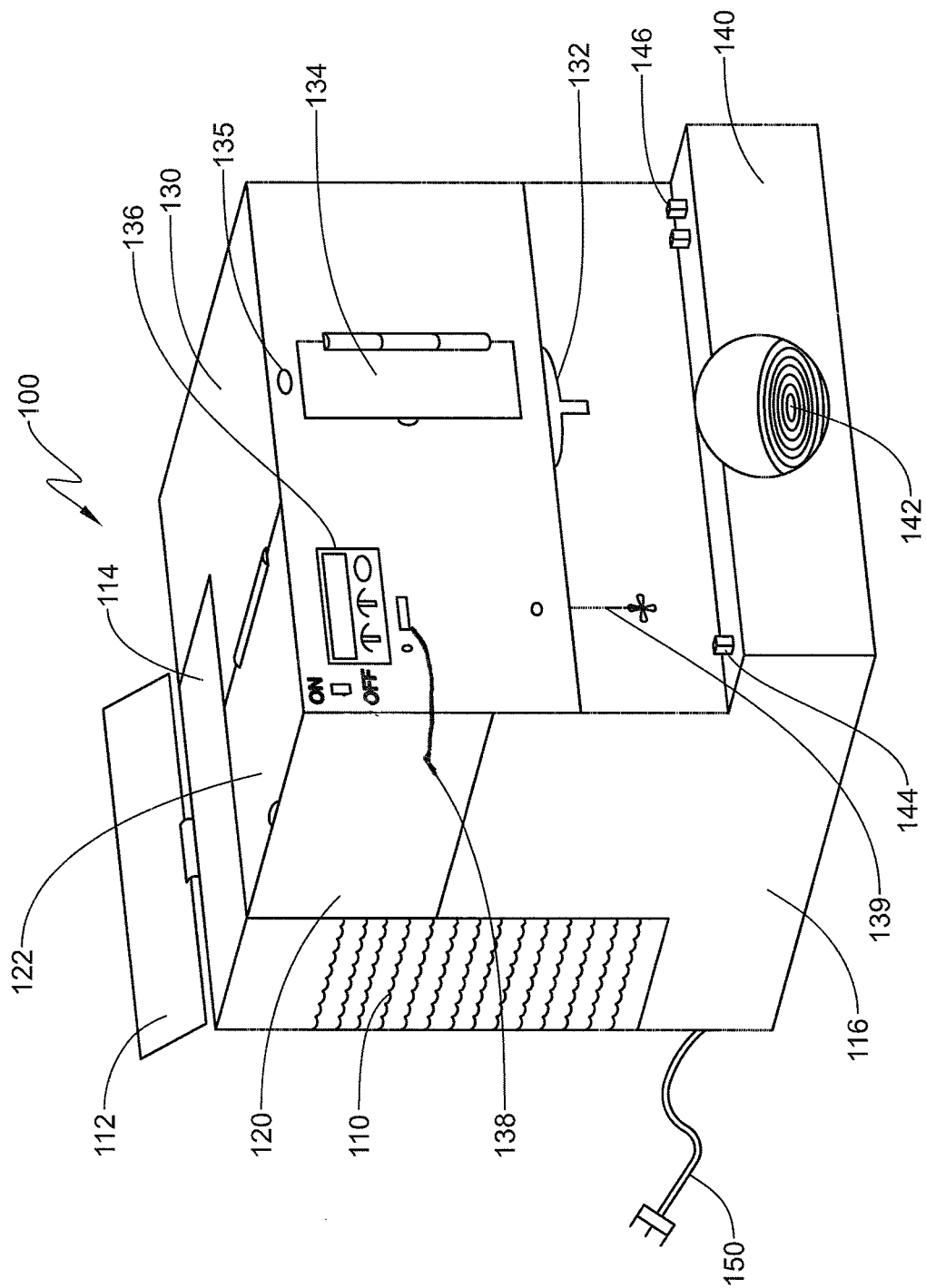
FIG. 1 is a front view perspective diagrammatic illustration of an exemplary embodiment of an appliance of the present disclosure.

Before describing various embodiments of the appliance, it is helpful to provide a brief description of a method of using it. To prepare the nasal irrigation appliance 100 for use, the removable Water Storage Tank 110 is filled with non-sterile water, such as tap water, and a preferably pharmaceutical grade mixture of sodium chloride and sodium bicarbonate granules is placed in the Bulk Sodium Container 120. A user turns on the appliance 100 and sets the desired water temperature, water volume, and sodium concentration using the controls provided in a Control Panel 136, and places a nasal irrigation delivery vessel (not shown) on the Dispensing Tray 140 under the Main Dispensing Unit 130.

Pressing a Prepare control in the Control Panel 136 turns on the motor/pump elements 240 and pumps the user-specified amount of water from the Water Storage Tank 110 through a sensor such as volumetric flow meter 230, for example, to the Water Heating Chamber 210. Pressing a Prepare button on the controller 136 panel also initiates measurement of the sodium from the Bulk Sodium Container 120 to the Dosage Cartridge 620 in preparation for dispensing. A Ready indicator 138 is activated when the desired amount of sodium mixture is loaded in the Dosage Cartridge 620 and the water in Water Heating Chamber 210 registers the desired temperature. When the Ready indicator 138 is active a Dispense control of controller 136 can be engaged to dispense the sodium mixture from the Dosage Cartridge 620 to the Main Dispensing Unit 130 and into a user-supplied nasal irrigation vessel, and then dispenses the sanitized, heated volume of water through an aseptic dispense valve 132 of the Main Dispensing Unit 130. Alternative embodiments of appliance 100 provide an Agitation Wand 139. The user can place the Agitation Wand 139 in the dispensed solution to further mix the sodium granules into the water. The Dispensing Tray 140 provides an indicator such as Receptacle 142 where the sodium and water will be dispensed to help the user align the nasal irrigation vessel with nozzle 132 of the Main Dispensing Unit 130, and provides a reservoir as a safeguard to contain at least one dosage of the sodium mixture and one volume of water should there be no vessel under the main dispensing unit 130 when the Dispense control is activated. The Dispensing Tray 140 provides a pop-up indicator 144 to show when the basin is full, and allows for easy removal and emptying of the tray. The Dispensing Tray 140 also can be used for storage of nasal irrigation delivery vessels.

Detailed Description of the Nasal Irrigation Appliance

Turning now to the appliance itself, FIG. 1 is an overview of a specific exemplary embodiment of the appliance as it appears from the front. The apparatus 100 includes Housing 116, a Sodium Storage, Measurement, and Delivery System (see FIGS. 1 and 3-8), a Water Storage, Heating, and Filtration System (see FIGS. 2 and 9), a Main Dispensing Unit 130, and a Dispensing Tray 140 which provides a receptacle to hold a nasal irrigation vessel (not shown), all of which are further described below, and further includes a controller 136, such as a panel with controls for the user to turn on the power 150 and customize the sodium solution that will be dispensed.

Appliance 100 provides additional features in specific exemplary embodiments, such as Water Storage Tank Lid 112 (which selectively opens to reveal opening 114 to fill tank 110 with water, and closes to inhibit evaporation), Bulk Sodium Container Lid 122, Pegs 146 to retain inverted components of a nasal irrigation vessel when not in use on Tray 140, Filter Change Indicator 135 and Filter Access 134.

Figure 2:
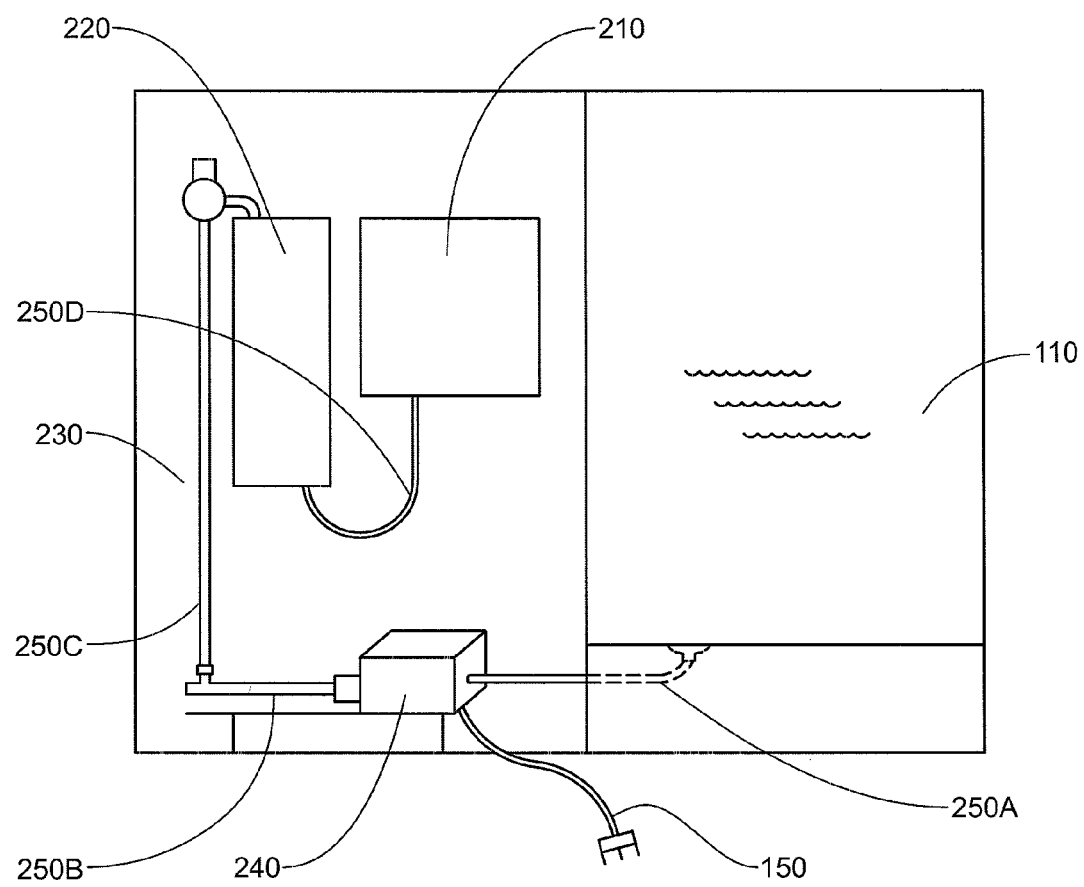
FIG. 2 is a partially cut-away back view diagrammatic illustration of an exemplary embodiment of the appliance of FIG. 1.

FIG. 2 is a cut away back view diagrammatic illustration of an exemplary embodiment of the appliance of FIG. 1. Water Storage Tank 110 is in fluid communication with Water Heating Chamber 210. Room temperature tap water, for example, is transported from Tank 110 to Heating Chamber 210 with Motor/Pump Assembly 240. The water is heated upon initiation of heating with Controller 136 to a pre-determined temperature and then pumped through Filter 220 to Main Dispensing Unit 130 after the water has achieved the pre-determined temperature. Sensor 230 automatically shuts off the supply of water when it detects that a pre-determined volume (set with Controller 136) has passed. Conduits 250A, 250B, 250C, 250D facilitate transport of the water through the system.

Figure 3:
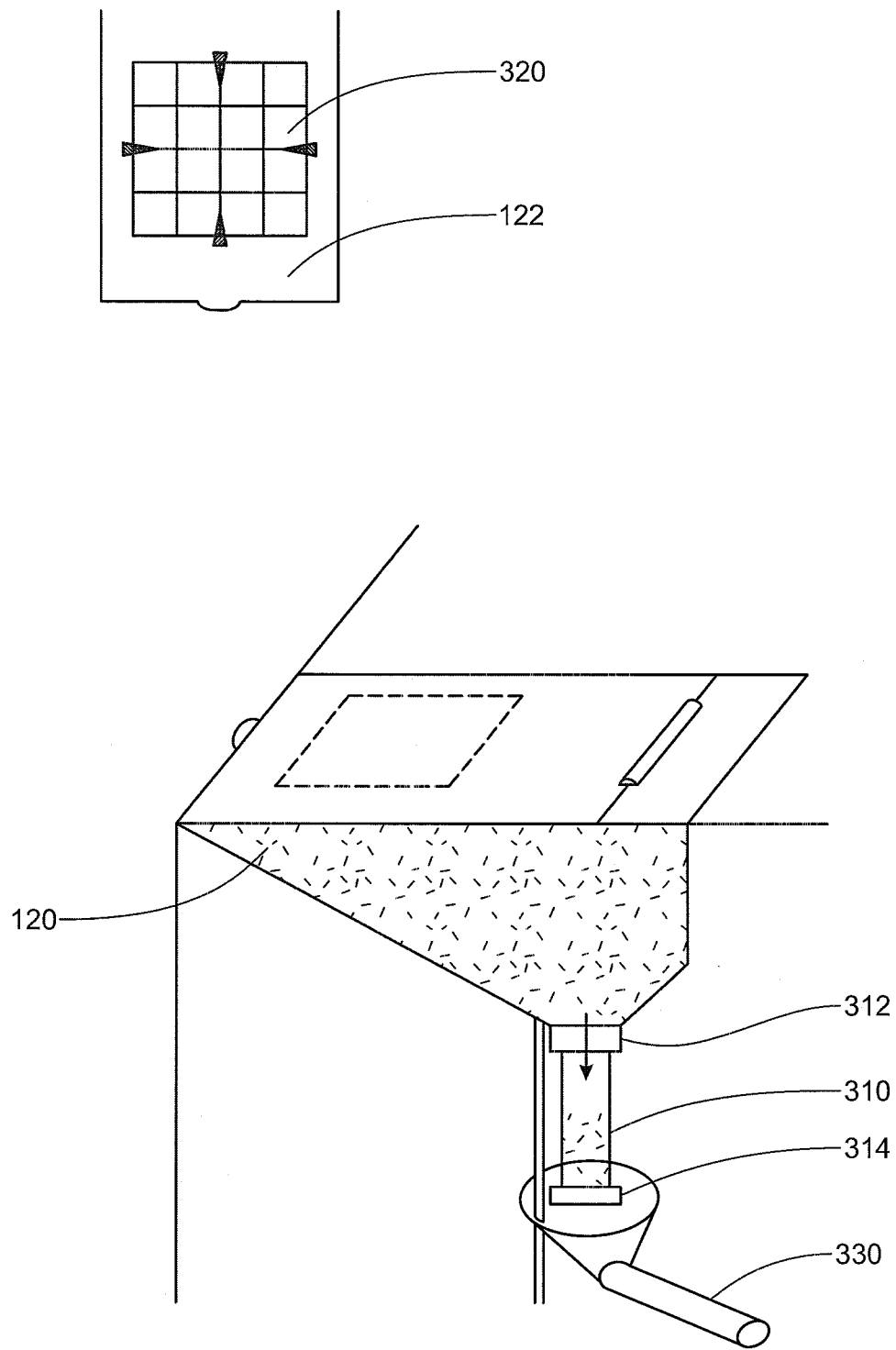
FIG. 3 is a front cut-away partially exploded view perspective diagrammatic illustration of a detail of the appliance of FIG. 1 for an exemplary embodiment to deliver a predetermined quantity of sodium salt.

FIG. 3 illustrates an exemplary embodiment of a Sodium Salt Storage, Measurement, and Delivery System of this disclosure. The bulk system provides a Bulk Sodium Salt Container 120 for the storage of a sodium chloride and sodium bicarbonate (preferably of pharmaceutical grade) granular mixture, provides a means for measuring a desired dosage of the sodium granules, provides for a means of storing a desired dosage of the sodium granules, and dispenses the desired dosage of sodium granules through a Funnel Cup Conveyer 330 and through the Main Dispensing Unit 130 to the target area 142 of the Dispensing Tray 140. The interior of the Bulk Sodium Container 120 is sloped such that the sodium granules collect in a narrow, flat area at the bottom of the container, from where the sodium is measured into a Dosage Cartridge 310. Dispense Plates 312/314 control movement of the sodium granules between the Bulk Sodium Salt Container 120 and the Dosage Cartridge 310 and between the Dosage Cartridge 310 and the Main Dispensing Unit 130. The interior side of Bulk Sodium Salt Container Lid 122 is outfitted with a replaceable Moisture Absorption Pad 320 to help keep the stored sodium granules dry.

Figure 4:
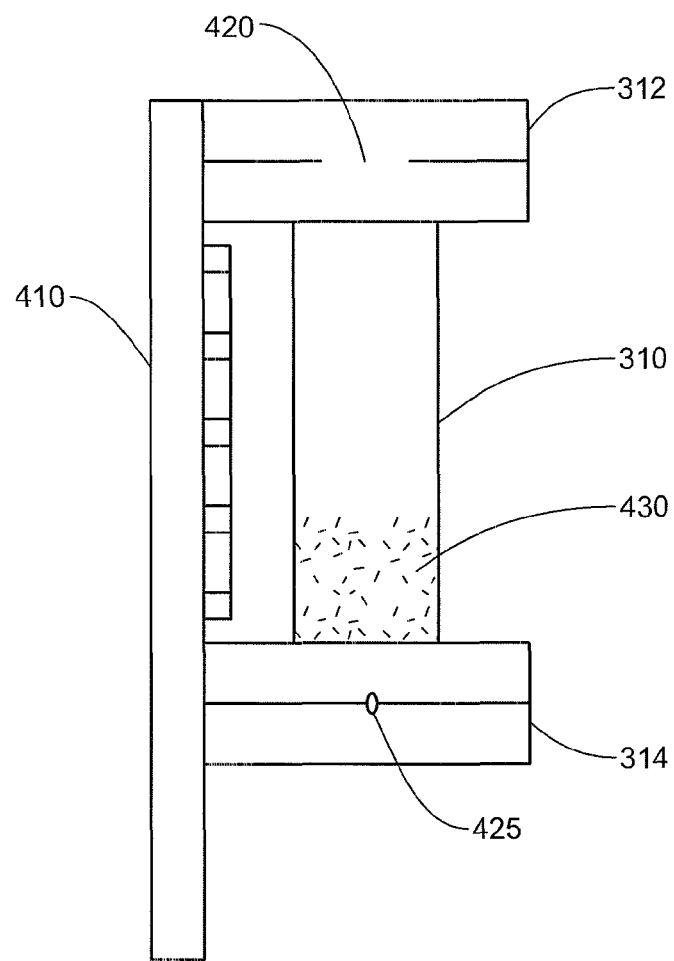
FIG. 4 is a side view diagrammatic illustration of the sodium salt dose cartridge of FIG. 3.

Three exemplary means for measuring the per-determined amount of sodium granules are described herein. One exemplary means is illustrated in FIG. 4. The Dosage Cartridge 310, mounted to Support 410, is outfitted with sensors (not shown) to detect the volume of granules that is released from the Bulk Sodium Salt Container 120 to the Dosage Cartridge 310 through open Dispense Plate Aperture 420, closing the Dispense Plate 312 when the volume reaches the preferred dosage set in Control Panel 136. Dispense Plate 314 opens to dispense the measured bulk quantity through an outlet to the Main Dispensing Unit 130.

Figure 5:
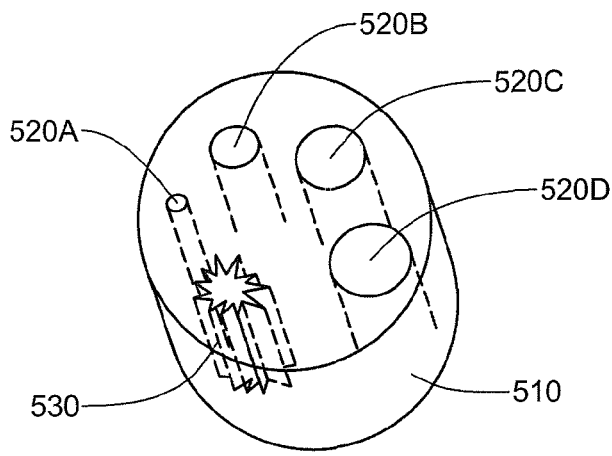
FIG. 5 is a top view perspective diagrammatic illustration of an alternative exemplary embodiment of a sodium salt dosing mechanism of an appliance of the present disclosure.

FIG. 5 illustrates another exemplary means. The Dosage Cartridge 510 contains individual chambers (such as shown by Dispensing Holes 520A, 520B, 520C, and 520D) to measure the smallest to largest dosage of sodium appropriate for creating an isotonic or hypertonic saline solution, and the Dosage Cartridge 510 is rotated with Positioner 530 perpendicular to the Bulk Sodium Salt Container 120 to align the Dispensing Hole 520A, 520B, 520C, 520D with the appropriately sized chamber according to the user's selection in the Control Panel.

Figure 6:
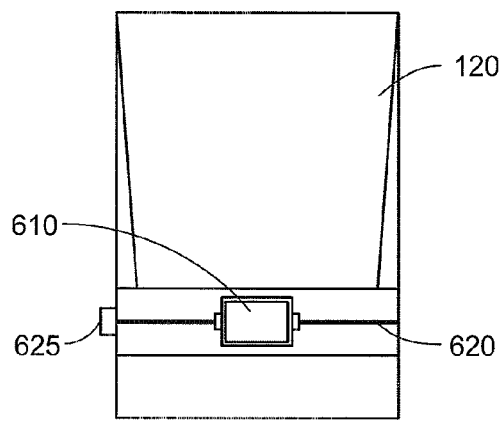
FIG. 6 is a front view diagrammatic illustration of a sodium salt dispenser of the exemplary embodiment of the appliance of FIG. 1.
Figure 7:
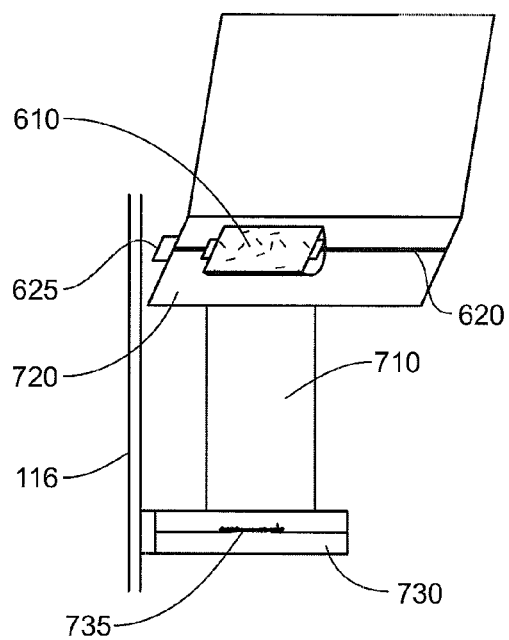
FIG. 7 is a front view diagrammatic illustration of the sodium salt dispenser of FIG. 6 in an open position.
Figure 8:
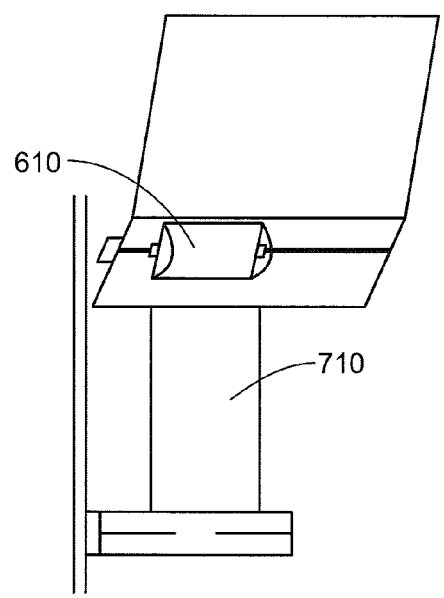
FIG. 8 is a front view diagrammatic illustration of the sodium salt dispenser of FIG. 6 in a closed position.

FIGS. 6-8 illustrate yet another exemplary embodiment. A Capsule 610 of the smallest desirable dosage (approximately 0.5 g, for example) located at the bottom 720 of the Bulk Sodium Salt Container 120. Capsule 610 rotates on Axel 620 by Actuator 625 between Bulk Sodium Salt Container 120 and Dosage Cartridge 710 to dispense the sodium granules into the Dosage Cartridge 710, filling up and repeating the process for larger dosage selections. Bulk sodium is transferred to Main Dispensing Unit 130 by opening Aperture 735 in Plate 730.

Figure 9:
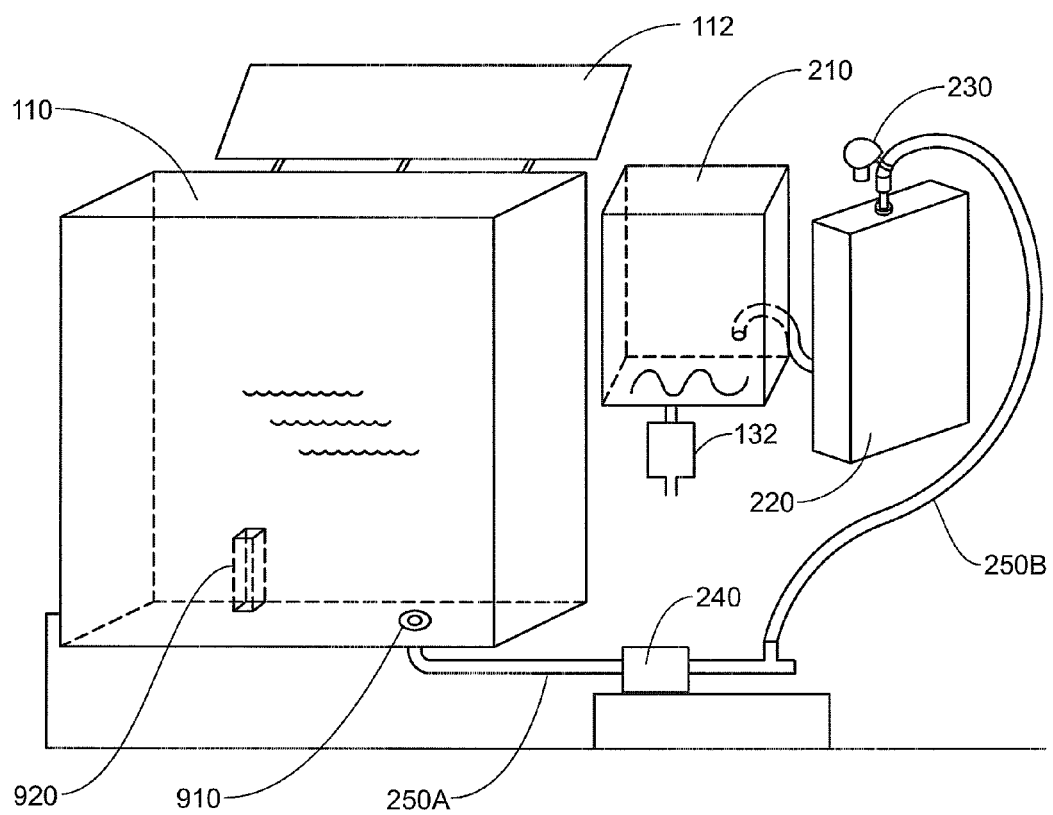
FIG. 9 is a schematic diagrammatic illustration of an alternative exemplary embodiment of the water treatment of an appliance of the present disclosure.

The Water Storage, Filtration, and Heating System is further illustrated in FIG. 9. A removable Water Storage Tank 110 that is capable of holding enough water for approximately seven nasal, for example, irrigation cleanings (840 mL to 1.7 L). Water Storage Tank 110 preferably contains a Float Level 920 to detect when the tank water level is low, and contains a Water Valve and Seal 910 that provides water to the Motor and Pump 240. The water is pumped through a sensor, such as a Volumetric Flow Meter with Solenoid Valve 230 until the dosage volume specified in the Control Panel 136 setting (120 mL to 240 mL) is reached. The dosage of water is filtered through a Water Filter 220 that has porosity small enough to remove pathogenic microorganisms such as the *Naegleria fowleri* (1 micron, for example) and through an aseptic connector to a thermostatically controlled Water Heating Chamber 210. When the water in the Water Heating Chamber 210 reaches the temperature set in the Control Panel 136, a Ready indicator 138 on the front panel is turned on. When a Dispense control is activated on Panel 136, the heated water is dispensed through an aseptic Dispense Valve 132 within the Main Dispensing Unit 130.

Figure 10:
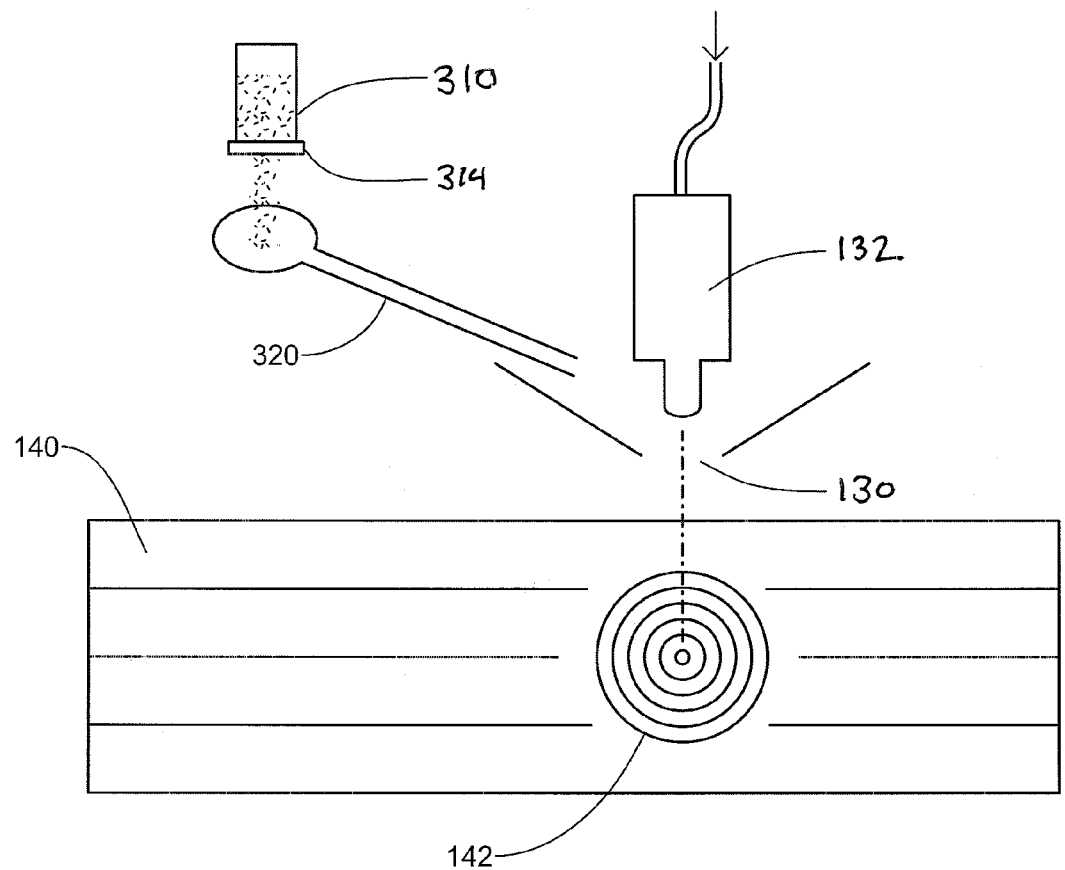
FIG. 10 is a schematic diagrammatic illustration of an exemplary embodiment of a main dispensing unit of an appliance of the present disclosure.

The Main Dispensing Unit of FIG. 10 provides a means for delivering the desired dose of both the sodium granules and heated water to a nasal irrigation vessel. The Main Dispensing Unit 130 and Dispensing Tray 140 accommodate a variety of popular nasal irrigation vessels, such as ceramic or plastic Neti pots, plastic squeeze bottles, and pulsatile flow-based delivery vessels. The Dispensing Tray 140 sits over a catch basin or reservoir that is designed to hold at least one dosage of sodium granules and water volume should the saline solution be dispensed with no delivery vessel in place or if the irrigation vessel overflows. A Indicator 144, such as a pop-up, for example, shows when the basin of Tray 140 is full, and the perforated pattern of Tray 140 shows the user where the opening of the nasal irrigation delivery vessel should be located to receive the dispensed sodium and water. The Dispensing Tray 140 can serve as a drying area for the irrigation delivery vessel and provides Pegs 146 for holding delivery vessel elements such as caps and tubes. The Dispensing Tray 140 can be removed to allow emptying of the basin.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus the following claims are hereby incorporated into the Detailed Description, with each claim standing on its own as a separate embodiment.

The description has made reference to several exemplary embodiments. It is understood, however, that the words that have been used are words of description and illustration, rather than words of limitation. Changes may be made within the purview of the appended claims, as presently stated and as amended, without departing from the scope and spirit of the disclosure in all its aspects. Although description makes reference to particular means, materials and embodiments, the disclosure is not intended to be limited to the particulars disclosed; rather, the disclosure extends to all functionally equivalent technologies, structures, methods and uses such as are within the scope of the appended claims.

What I claim is:

1. A method for preparing and dispensing a nasal irrigation solution, the method comprising the steps of:

providing an apparatus for preparing and dispensing a nasal irrigation solution, the apparatus further comprising:
   a container for bulk sodium salts,
   a storage tank for water,
   a main dispensing unit in fluid communication with the container for bulk sodium salts and the storage tank for water,
   a bulk sodium salts measurer connected to the container for bulk sodium salts to deliver a predetermined amount of sodium salt to the main dispensing unit,
   a water heating chamber in fluid communication with the water storage tank and the main dispensing unit,
   a sensor between the water heating chamber and the main dispensing unit to deliver a predetermined amount of water to the main dispensing unit,
   a filter between the storage tank for water and the main dispensing unit, the filter being capable of filtering amoeba from the water,
   a receptacle for a nasal irrigation vessel, the receptacle being positioned such that a nasal irrigation vessel receives the saline solution from the main dispensing unit, and
   at least one controller for a user of the appliance to set the parameters of the saline solution and to initiate preparation and delivery of the saline solution through the main dispensing unit, whereby the appliance prepares the saline solution in the main dispensing unit to a predetermined temperature and concentration of sodium salts and delivers the saline solution to the receptacle for the nasal irrigation vessel;

providing the container for bulk sodium salts with predetermined amount of bulk sodium salts;

providing the storage tank for water with predetermined amount of water;

activating the apparatus with the controller such that the appliance prepares the saline solution in the main dispensing unit to a predetermined temperature and concentration of sodium salts and delivers the saline solution to the receptacle for the nasal irrigation vessel; and irrigating nasal passages with the saline solution from the nasal irrigation vessel.

2. The method of claim 1, further comprising providing the apparatus wherein the bulk sodium salts measurer of the apparatus comprises a dosage cartridge, and measuring the dose of sodium salts with the dose cartridge.

3. The method of claim 2, further comprising providing the apparatus wherein the dosage cartridge of the apparatus comprises a plurality of chambers and a selectively positionable plurality of dispensing holes whereby the dose of sodium salts is pre-determined by the dispensing hole positioned over a chamber, and positioning a dispensing hole for a pre-determined dose of sodium salts.

4. The method of claim 2, further comprising providing the apparatus wherein the bulk sodium salts measurer of the apparatus comprises a sensor to detect the pre-determined amount of sodium salts, and sensing the pre-determined amount of sodium salts with the sensor.

5. The method of claim 1, further comprising providing the apparatus wherein the apparatus of the method further comprises a conveyor to deliver the pre-determined amount of sodium salts to the main dispensing unit, and delivering the pre-determined amount of sodium salts to the main dispensing unit with the conveyor.

6. The method of claim 1, further comprising providing the apparatus wherein the apparatus of the method further comprises a perforated tray to house the receptacle, and housing the receptacle in the perforated tray.

7. The method of claim 6, further comprising providing the apparatus wherein the tray of the apparatus further comprises a vessel retainer to retain an irrigation vessel when not in use, and retaining the irrigation vessel when not in use in the vessel retainer.

8. The method of claim 7, further comprising providing the apparatus wherein the tray of the apparatus is selectively removable and further comprising the step of selectively removing the tray.

9. The method of claim 6, comprising providing the apparatus wherein the apparatus further comprises a catch basin under the tray.

10. The method of claim 9, further comprising providing the apparatus wherein the catch basin further comprises a full indicator.

11. The method of claim 1, further comprising providing the apparatus wherein the water storage tank is selectively removable, and selectively removing the water storage tank.

12. The method of claim 1, further comprising providing the apparatus that further comprises a power source connected to a pump, the pump being in fluid communication with the storage tank for water, and connecting the pump to the power source.

13. The method of claim 1, further comprising providing the apparatus wherein the sensor to deliver a pre-determined amount of water to the main dispensing unit comprises a volumetric flow sensor, and determining the pre-determined amount of water to deliver to the main dispensing unit with the volumetric flow sensor.

14. The method of claim 1, further comprising providing the apparatus wherein the filter pore size is less than or equal to 1 micron.

15. A method for preparing and dispensing a nasal irrigation solution, the method comprising the steps of:
   providing an apparatus for preparing and dispensing a nasal irrigation solution, the apparatus further comprising:
   a container for bulk sodium salts,
   a selectively removable storage tank for water,
   a main dispensing unit in fluid communication with the container for bulk sodium salts and the storage tank for water,
   a power source connected to a pump, the pump being in fluid communication with the storage tank for water,
   a bulk sodium salts measuring sensor connected to the container for bulk sodium salts by a conveyor to deliver a predetermined amount of sodium salt to the main dispensing unit,
   a water heating chamber in fluid communication with the water storage tank and the main dispensing unit,
   a volumetric flow sensor between the water heating chamber and the main dispensing unit to deliver a predetermined amount of water to the main dispensing unit,
   a filter between the storage tank for water and the main dispensing unit, the filter being capable of filtering amoeba from the water,
   a selectively removable perforated tray having a receptacle for a nasal irrigation vessel, the receptacle being positioned such that a nasal irrigation vessel receives the saline solution from the main dispensing unit,
   a catch basin under the perforated tray, the basin having a full indicator,
   a vessel retainer, and
   at least one controller for a user of the appliance to set the parameters of the saline solution and to initiate preparation and delivery of the saline solution through the main dispensing unit, whereby the appliance prepares the saline solution in the main dispensing unit to a predetermined temperature and concentration of sodium salts and delivers the saline solution to the receptacle for the nasal irrigation vessel,
   providing the container for bulk sodium salts with pre-determined amount of bulk sodium salts;
   providing the storage tank for water with predetermined amount of water;
   activating the apparatus with the controller such that the appliance prepares the saline solution in the main dispensing unit to a predetermined temperature and concentration of sodium salts and delivers the saline solution to the receptacle for the nasal irrigation vessel; and
   irrigating nasal passages with the saline solution from the nasal irrigation vessel.

\* \* \* \* \*